United States Patent [19]

Berka et al.

[11] Patent Number: 5,667,990
[45] Date of Patent: Sep. 16, 1997

[54] ASPERGILLUS EXPRESSION SYSTEM

[75] Inventors: Randy Michael Berka, Davis; Wendy Yoder, Winters; Shinobu Takagi; Karuppan Chettier Boominathan, both of Davis, all of Calif.

[73] Assignee: Novo Nordisk Biotech, Inc., Davis, Calif.

[21] Appl. No.: 458,023

[22] Filed: Jun. 1, 1995

Related U.S. Application Data

[63] Continuation of Ser. No. 161,675, Dec. 1, 1993, abandoned.

[51] Int. Cl.$^6$ .......................... C12P 21/02; C12N 15/11; C12N 1/15; C07H 21/04
[52] U.S. Cl. ................ 435/69.1; 435/172.3; 435/254.3; 536/23.2; 536/23.74
[58] Field of Search ................... 435/254.3, 69.1, 435/172.3; 536/23.2, 23.74

[56] References Cited

PUBLICATIONS

Cheng et al. (1990) Curr.Genet. 18, 453–456.
Devchand et al. (1991) J. Biotech. 17, 3–10.
Kaan et al. (1990) Enzyme Microb. Technol. 12(2), 127–131.
Morosoli et al. (1992), Gene 117, 145–150.
Murao et al. (1988). in "Methods in Enzymol, vol. 160", eds. Wood et al., pp. 274–299, Academic Press, N.Y.
Ooi et al. (1990) Curr. Genet. 18, 217–222.
Teeri et al. (1987) Gene 51, 43–52.
Tsuchiya et al. (1992) Biosci. Biotech Biochem. 56(11) 1849–1853.
Yamaguchi et al. (1991) Gene 103, 61–67.

*Primary Examiner*—James Ketter
*Assistant Examiner*—John S. Brusca
*Attorney, Agent, or Firm*—Steve T. Zelson, Esq.; James Harrington, Esq.

[57] ABSTRACT

The present invention relates to a novel expression system in which *A. japonicus*-type species are used as host cells for expression of heterologous proteins.

28 Claims, No Drawings

ASPERGILLUS EXPRESSION SYSTEM

This application is a continuation of application Ser. No. 08/161,675, filed Dec. 1, 1993, abandoned, the contents of which are incorporated herein by reference.

FIELD OF THE INVENTION

The present invention relates to host cells useful in the production of recombinant proteins. In particular, the invention relates to fungal host cells of the genus Aspergillus, which can be used in the high-level expression of recombinant proteins, especially enzymes.

BACKGROUND OF THE INVENTION

The use of recombinant host cells in the expression of heterologous proteins has in recent years greatly simplified the production of large quantities of commercially valuable proteins, which otherwise are obtainable only by purification from their native sources. Currently, there is a varied selection of expression systems from which to choose for the production of any given protein, including prokaryotic and eukaryotic hosts. The selection of an appropriate expression system will often depend not only on the ability of the host cell to produce adequate yields of the protein in an active state, but also to a large extent may be governed by the intended end use of the protein.

Although mammalian and yeast cells have been the most commonly used eukaryotic hosts, filamentous fungi have now begun to be recognized as very useful as host cells for recombinant protein production. Among the filamentous fungi which are currently used or proposed for use in such processes are *Neurospora crassa, Acremonium chrysogenum, Tolypocladium geodes, Mucor circinelloides* and *Trichoderma reesei*. In addition, certain species of the genus Aspergillus have been used effectively as host cells for recombinant protein production. Aspergillus is a deuteromycete fungus characterized by an aspergillum consisting of a conidiospore stipe terminating in a vesicle, which in turn bears one or two layers of synchronously formed specialized cells, variously referred to as sterigmata or phialides, and asexually formed spores referred to as conidia. The species *Aspergillus nidulans* has been reported to be transformed with recombinant plasmids (Ballance, et al. Biochem. Biophys. Res. Comm. 112: 284–289, 1983), but transformation was found to occur at fairly low frequency. Both *Aspergillus niger* and *Aspergillus oryzae* have also been described as being useful in recombinant production of proteins. However, other species of Aspergillus have not been shown to be useful in expression of heterologous protein, and in fact, because of poor expression and/or excessive production of proteases or mycotoxins, not all species of Aspergillus are suitable as host cells for this purpose, nor is this ability predictable from one species to the next. An ideal expression system is one which is substantially free of protease and mycotoxin production and large amounts of other endogenouslymade secreted proteins, and which is capable of higher levels of expression than known host cells. The present invention now provides new Aspergillus expression systems which fulfill these requirements.

SUMMARY OF THE INVENTION

The present invention provides a host cell of an *Aspergillus japonicus*-type species, such as the species *Aspergillus japonicus, Aspergillus aculeatus* or *Aspergillus japonicus* var. *aculeatus*, which host cell contains a nucleic acid sequence encoding a heterologous protein. By "heterologous protein" is meant one which is not native to the host cell, or a native protein in which modifications have been made to alter the native sequence. In a preferred embodiment the protein is a heterologous enzyme. The nucleic acid sequence is operably linked to a suitable promoter sequence, which is capable of directing transcription of the nucleic acid sequence in the chosen host cell.

The invention also relates to a method for production of recombinant proteins, the method comprising culturing a host cell of one of the aforementioned species, which host cell contains a nucleic acid sequence encoding a heterologous protein, under conditions conducive to expression of the protein, and recovering the protein from the culture. In a preferred embodiment, the protein is a fungal protein, most preferably a fungal enzyme.

The host cells and methods of the present invention are unexpectedly more efficient in the recombinant production of certain fungal enzymes than are other known Aspergillus species, such as *A. oryzae*.

DETAILED DESCRIPTION OF THE INVENTION

The species *A. japonicus, A. japonicus* var. *aculeatus*, and *A. aculeatus* all belong to the Nigri Section of the genus Aspergillus. The members of the section Nigri, as exemplified by *Aspergillus niger*, are characterized by radiate conidial heads and conidial masses in shades of black; globose vesicles; stipes which are smooth and hyaline, or pigmented below the vesicle; metulae present or absent, and often pigmented ("The Genus Aspergillus", by K. B. Raper and D. I. Fennel, The Williams & Wikins Company, Baltimore, 1965). Mutants of these strains differing in spore color and ornamentation, or other micromorphological characters also would be included in this section. Within the Nigri section of the genus Aspergillus, the delimitation of taxa is subject to debate, due to variation in colony color and conidiogenous structures on which the major classification schemes are primarily based (i.e., Raper and Fennel, supra). The *A. japonicus*-related taxa recognized by Raper and Fennel are *A. japonicus* and *A. aculeatus*. Samson and Gams("Advances In Penicillium and Aspergillus Systematics", Samson and Pitt, eds., 1985) recognize *A. japonicus* only, and Al-Mussallam("Revision of the Black Aspergillus Species", Ph.D. thesis, University of Utrecht, 1980) recognizes *A. japonicus* var. *japonicus* and *A. japonicus* var. *aculeatus*.

The species *A. japonicus* is generally characterized by uniseriate sterigmata, and globose to subglobose, conspicuously echinulate conidia. The vesicles are commonly 20–35μ, but range from 15–45μ. The species was first described in Saito, Botan. Mag. 20: 61–63, 1906. More specifically, the species is characterized as follows: Colonies on Czapek's solution agar growing rapidly at room temperature (24°–26° C.), in most strains 5.0 to 6.0 cm in diameter in 10 days, but in occasional strains less, consisting of a dense, white, irregularly wrinkled basal mycelium which tardily gives rise to a dense strand of conidial structures in purple-brown or purple-black shades, occasional strains producing abundant white to cream-colored globose sclerotia in central colony areas; reverse at first uncolored by later becoming purple drab and occasionally with a slight yellow-green tinge; exudate lacking; odor sometimes quite strong but not distinctive. Conidial heads variable, small, radiate or split into few indistinct columns, rarely exceeding 300μ in diameter at 10 days but in age sometimes distinctly columnar and up to 600–700μ long or split into two divergent columns of similar length; conidiophores smooth or with a limited surface granulation, colorless or slightly pigmented particularly just below the vesicle, sinuous, mostly 500 to 1000μ by 5 to 10μ but varying greatly in these dimensions; vesicles somewhat colored in brownish yellow shades, often somewhat elongate but in older or larger heads more nearly globose, mostly 20 to 30μ by 25 to 35μ by ranging from less than 15 to 45μ in diameter, in normal heads fertile over most of their surface but in small heads at the apex only; sterigmata uniseriate, 5.5 to 8.0μ by 3.0 to 4.5μ, rarely swollen to double their normal size; conidia mostly globose, occasionally subglobose, strongly echinulate, with echines discrete and regularly space, commonly 0.5μ long, occasionally longer, spore bodies mostly 3.0 to 3.5μ; sclerotia produced abundantly but tardily by some strains, white to cream, globose, up to 500μ in diameter. Colonies on malt extract agar growing rapidly, 7 to 8 cm in diameter in 10 days at room temperature, more quickly and heavily sporulating than on Czapek's; conidial heads usually larger than on Czapek's and split into conspicuous columnar masses, commonly reaching diameters of 500μ in 10 days and showing a narrower range of vesicle and stalk measurements; sterigmata and conidia as described above. The subspecies A. japonicus var. aculeatus is distinguished by the following characteristics: colonies on Czapek agar attaining 5.5 cm diameter in 14 days, consisting of fairly compact, irregularly wrinkled, white basal felt; some strains produce floccose aerial mycelium; reverse uncolored becoming brown with age; conidial heads produced in mass, purplish-brown near Quaker Drab and Dusky Drab, globose to radiate, splitting into well-defined divergent coles, 200–300μ in diameter; conidiophore stalked smooth, hyaline or slightly pigmented at the apex, erect, from 350–4500μ, usually between 1000–2000μ long, 9.0–13.5μ wide; vesicles brown, 30–90μ, usually 45–67μ in diameter, bearing crowded philiades over the entire surface of large vesicles and over the upper three quarters in smaller ones; philiades 7.5–10×4–5μ; conidia hyaline to brown, conspicuously echinulate, subglobose but mostly ellipsoidal, 4–5× 3.5–4.5μ; sclerotia produced abundantly in some strains, in concentric zones, globose to subglobose, 450–675μ, but up to 800μ in diameter.

The closely related species A. aculeatus is characterized generally by uniseriate sterigmata, and subglobose to definitely elliptical, conspicuously echinulate conidia. The vesicles are usually 60–80μ, ranging from 35 to 100μ. More specifically, the species is defined as follows: colonies on Czapek's solution agar growing rapidly at room temperature (24°–26° C.), 5 to 6 cm in diameter in 12 days, plane, producing a dense stand of conidial structures, heavily sporing throughout in purple-brown or purple-black shades often with a slight gray-tan surface "bloom"; reverse uncolored or in fairly conspicuous yellow shades to near black at colony center, yellow pigment diffusible; exudate and odor lacking; white to cream colored sclerotia produced by occasional strains, most abundant at colony centers and at contiguous margins. Conidial heads globose at first, then splitting into relatively few compact divergent columns, reaching diameters up to 1 mm but commonly 500 to 700μ, shattering easily with columns deciduous, individual heads often variable in color with conidia nearest the vesicles light tan; conidiophores uncolored or slightly brownish below the vesicles, usually 1–2 mm by 9 to 13μ but up to 2.5 mm long and 18 to 29μ in diameter with walls up to 2.0 to 2.5μ thick, smooth or occasionally showing a limited deposit of granular material; vesicles often somewhat elongate when young, globose or nearly so when fully developed, heavy walled, commonly pigmented in brown shades and 60 to 80μ in diameter but ranging from 35 to 100μ, fertile over the entire surface; sterigmata in a single series, closely packed, 6.5 to 10.0μ by 3.0 to 4.4μ; conidia ranging from definitely elliptical to globose or nearly so, varying with the strain or within a single strain, mostly 3.5 to 4.0μ by 4.5 to 5.0μ, but with occasional cells measuring as much as 4 by 7μ, in mounts showing a purplish tinge, conspicuously echinulate with echines discrete and rather widely spaced. This species was first described in Iizuka, J. Agr. Chem. Soc. Japan 27: 806, 1953.

It will be understood that throughout the specification and claims the use of the term "A. japonicus-type species" refers not only to organisms encompassed in the aforementioned three species, but also includes those species which have previously been or currently are designated as other species in alternate classification schemes, but which possess the same morphological and cultural characteristics defined above, and may be synonyms of A. japonicus, A. japonicus var. aculeatus or A. aculeatus. For example, synonyms of A. japonicus/A. japonicus var. japonicus include (but are not limited to) A. japonicus Saito var. capillatus Nakazawa, Takeda and Suematsu, A. malvaceus Mosseray, A. atrovioloaceus Mosseray, A. atrofuscus Mosseray, A. violaceofuscus Gasperini, A. brunneo-violaceus Bat. and Maia (Al-Mussallam, supra), and A. japonicus var. atrofuscus Iizuka (J. Agr. Chem. Soc. Japan 27: 807, 1953). Synonyms of A. aculeatus/A. japonicus var. aculeatus include (but are not limited to) A. yezoensis Sasaki (Al-Musallam, supra), A. japonicus var. viridiflavus Iizuka (J. Agr. Chem. Soc. Japan 27: 807, 1953), and A. violaceo fuscus Gasperini (Atti. Soc. Toscana Sci. Nat. Pisa, 8(2): 326–328, 1887).

Initial determination of candidate host cells is made by evaluation of the level of protease produced by the various isolates from over fifteen species in different taxonomic sections of the genus Aspergillus. This is accomplished by testing each isolate on a casein clearing plate assay at acidic, neutral and alkaline pH. Surprisingly, it is found that several members of the Section Nigri perform best in that they produced the smallest quantities of proteases, which could potentially cause degradation of any recombinant proteins produced. Based on this criterion, six species are chosen for further study, including A. japonicus, A. japonicus var. aculeatus, A. aculeatus, A. tamarii, A. carbonarius, and A. phoenicis.

Attempts to transform the selected species are then conducted. Initial efforts focus on use of standard A. oryzae transformation techniques (Christensen et al., Bio/Technology 6: 1419–1422, 1988; EP Appln. No. 87 103 806.3). In brief, cotransformants are obtained using the A. oryzae protocol for protoplasting, transformation and selection for amdS or hygromycin B (hygB) marker genes. Expression vectors contain the A. oryzae TAKA-amylase gene, and the transcription termination signals from the A. niger glucoamylase gene, in addition to a heterologous coding sequence. Transformation frequencies vary from less than one to approximately 10 per microgram of DNA. In co-transformation experiments with the expression vectors detailed in the following examples, the frequency of co-transformation ranges from 0–60%.

The transformed species are then observed to determine the level of expression of various heterologous enzymes. The heterologous enzymes tested include Humicola lanuginosa lipase (HLL), Humicola insolens xylanase (Xylanase), Humicola insolens cellulase (Cellulase), Coprinus cinereus peroxidase (CiP), and Candida antarctica lipase A. Surprisingly, the three species of the A. japonicus-like group showed the best expression for one or more of the enzymes, but in some cases, show better yield of enzyme than the control *A. oryzae* strains. In particular, a number of strains of each of *A. aculeatus*, *A. japonicus*, and *A. japonicus* var. *aculeatus* produce quite high levels of HLL (about one gram per liter) in shake flask culture. In addition, *A. japonicus* shows excellent production of xylanase in comparison with production of this enzyme in *A. oryzae* and *A. niger* strains. Moreover, *A. aculeatus* in a shake flask produces the *Candida antarctica* lipase A in the range of about 1.0 g/liter, which is about three to four times better than corresponding *A. oryzae* transformants grown under the same conditions. A summary of the results of these tests is provided in Table 2.

As the results clearly show, several isolates of each species are capable of expressing heterologous protein. Thus, it is understood that this ability is not limited to a single isolate or strain, but rather is a characteristic of this group of species as a whole. Those skilled in the art will recognize that other strains or isolates of these species can also be used in expression of heterologous expression. Many strains of each species are publicly available in the collections of the American Type Culture Collection (ATCC) 12301 Parklawn Drive, Rockville Md. 20852; Agricultural Research Service Culture Collection (NRRL) 1815 North University Street, Peoria, Ill. 61604; Fungal Genetics Stock Center (FGSC), Kansas; Deutsche Sammlung yon Mikroorganismen und Zellkulturen (DSM), Mascheroder Weg 1B, D-3300 Braunschweig, Germany; Institute of Applied Microbiology (IAM), Tokyo University 1-1,1-Chome, Yayoi, Bunkyo-ku, Tokyo 113, Japan; Institute for Fermentation (IFO), 17–85 Juso-honmachi 2-chome, Yodogawaku, Osaka 532, Japan; and Centraal Bureau voor Schimmelcultures (CBS), Oosterstraat 1, 3740 AG Baarn, Netherlands.

The skilled artisan will also recognize that the successful transformation of the host species described herein is not limited to the use of the vectors, promoters, and selection markers specifically exemplified. Generally speaking, those techniques which are useful in transformation of *A. oryzae*, *A. niger* and *A. nidulans* are also useful with the host cells of the present invention. For example, although the amdS and hygB selection markers are preferred, other useful selection markers include the argB (*A. nidulans* or *A. niger*), trpC (*A. niger* or *A. nidulans*), or pyrG (*A. niger* or *A. nidulans*) markers. The promoter may be any DNA sequence that shows strong transcriptional activity in these species, and may be derived form genes encoding both extracellular and intracellular proteins, such as amylases, glucoamylases, proteases, lipases, cellulases and glycolytic enzymes. Such suitable promoters may be derived from genes for *A. oryzae* TAKA amylase, *Rhizomucor miehei* aspartic proteinase, *A. niger* glucoamylase, *A. niger* neutral α-amylase, *A. niger* acid stable α-amylase, and *Rhizomucor miehei* lipase. Examples of promoters from genes for glycolytic enzymes are TPI, ADH, and PGK. The promoter may also be a homologous promoter, i.e., the promoter for a native *A. japonicus*-type gene. A preferred promoter according to the present invention is the *A. oryzae* TAKA amylase promoter. The TAKA amylase is a well-known α-amylase (Toda et al., Proc. Japan Acad. 58 Ser. B.: 208–212, 1982). The promoter sequence may also be provided with linkers for the purpose of introducing specific restriction sites facilitating ligation of the promoter sequence with the gene of choice or with a selected signal peptide or preregion. Terminators and polyadenylation sequences may also be derived from the same sources as the promoters. Enhancer sequences may also be inserted into the construct.

To avoid the necessity of disrupting the cell to obtain the expressed product, and to minimize the amount of possible degradation of the expressed product within the cell, it is preferred that the product be secreted outside the cell. To this end, in a preferred embodiment, the gene of interest is linked to a preregion such as a signal or leader peptide which can direct the expressed product into the cell's secretory pathway. The preregion may be derived from genes for any secreted protein from any organism, or may be the native preregion. Among useful available sources for such a preregion are a glucoamylase or an amylase gene from an Aspergillus species, an amylase gene from a Bacillus species, a lipase or proteinase gene from *Rhizomucor miehei*, the gene for the α-factor from *Saccharomyces cerevisiae*, or the calf prochymosin gene. Most preferably the preregion is derived from the gene for *A. oryzae* TAKA amylase, *A. niger* neutral α-amylase, *A. niger* acid stable α-amylase, *B. licheniformis* α-amylase, the maltogenic amylase from Bacillus NCIB 11837, *B. stearothermophilus* α-amylase, or *B. licheniformis* subtilisin. An effective signal sequence is the *A. oryzae* TAKA amylase signal, the *Rhizomucor miehei* aspartic proteinase signal and the *Rhizomucor miehei* lipase signal. As an alternative, the preregion native to the gene being expressed my also be used.

The gene for the desired product functionally linked to promoter and terminator sequences may be incorporated in a vector containing the selection marker or may be placed on a separate vector or plasmid capable of being integrated into the genome of the host strain. The vector system may be a single vector or plasmid or two or more vectors or plasmids which together contain the total DNA to be integrated into the genome. Vectors or plasmids may be linear or closed circular molecules. According to a preferred embodiment of the present invention, the host is transformed with two vectors, one including the selection marker and the other comprising the remaining heterologous DNA to be introduced, including promoter, the gene for the desired protein and transcription terminator and polyadenylation sequences.

The present host cell species can be used to express any prokaryotic or eukaryotic heterologous protein of interest, and is preferably used to express eukaryotic proteins. The species *A. japonicus* and *A. aculeatus* are particularly useful in that each has been approved for use in the food industry. (Regulatory Aspects of Microbial Food Enzymes, Third Edition, The Association of Microbial Food Enzyme Producers, Brussels, Belgium). Of particular interest for these species is their use in expression of heterologous proteins, especially fungal enzymes. The novel expression systems can be used to express enzymes such as catalase, laccase, phenoloxidase, oxidase, oxidoreductases, cellulase, xylanase, peroxidase, lipase, hydrolase, esterase, cutinase, protease and other proteolytic enzymes, aminopeptidase, carboxypeptidase, phytase, lyase, pectinase and other pectinolytic enzymes, amylase, glucoamylase, α-galactosidase, β-galactosidase, α-glucosidase, β-glucosidase, mannosidase, isomerase, invertase, transferase, ribonuclease, chitinase, and deoxyribonuclease. It will be understood by those skilled in the art that the term "fungal enzymes" includes not only native fungal enzymes, but also those fungal enzymes which have been modified by amino acid substitutions, deletions, additions, or other modifications which may be made to enhance activity, thermostability, pH tolerance and the like.

The present host cells may also be used in recombinant production of proteins which are native to the host cells. Examples of such use include, but are not limited to, placing an *A. japonicus*-type native protein under the control of a different promoter to enhance expression of the protein, to expedite export of a native protein of interest outside the cell by use of a signal sequence, or to increase copy number of a protein which is normally produced by the subject host cells. Thus, the present invention also encompasses such recombinant production of homologous proteins, to the extent that such expression involves the use of genetic elements not native to the host cell, or use of native elements which have been manipulated to function in a manner not normally seen in the host cell.

The invention is further illustrated by the following non-limiting examples.

I. Protease assays

More than fifty strains, from at least fifteen different species, are examined to determine the amount of protease produced by each isolate, and also to observe their extracellular protein profile. To prepare culture inoculum, 10 ml of sterile distilled water is added to one 7–10 day old culture of each strain in a 9 cm petri dish, and spores are scraped gently from the mycelia to make a dense suspension. 2.5 ml of the suspension is used to inoculate 100 ml of ASPO4 medium[ASPO4 medium comprises 1 g/l $CaCl_2$, 2 g/l yeast extract, 1 g/l $MgSO_4$, 5 g/l $KH_2PO_4$, 2 g/l citric acid, 0.5 ml Trace Metal solution (comprising 14.3 g/l $ZnSO_4.7 H_2O$, $CuSO_4.5H_2O$, 0.5 g/l $NiCl_2.6H_2O$, 13.8 g/l $FeSO_4.7H_2O$, 8.5 g/l $MnSO_4.H_2O$, and 3 g/l citric acid), 1 g/l urea, 2 g/l $(NH_4)_2SO_4$, 20 g/l maltodextrin (8 ml of a 25% stock, added after autoclaving) in tap water, pH adjusted to 4.5 or 6.5 before autoclaving, then pH 4.5 adjusted with 8 ml 0.1M citric acid per 100 ml after autoclaving]. Flasks are incubated at 30 and/or 37° C., shaking on an orbital shaker at 200 rpm, for 5 days, in continuous light. Supernatant from the culture broth of each is spun at 2500 rpm for 5 minutes, and used in the casein clearing plate assay, which determines the levels of proteases produced by various fungal species being evaluated as potential candidates for recombinant protein expression.

The casein plate clearing assay is conducted as follows. The plate medium is composed of 20 g/l skim milk, 20 g/l agarose, and 0.2M citrate-phosphate buffer for tests run at pH 5 and pH 7, and glycine NaOH buffer for tests run at pH 9. Milk powder is mixed with 100 ml of buffer and kept at 60° C. Agarose is mixed with 400 ml of buffer and autoclaved 5 minutes. After slight cooling, the warm milk mixture is added, and the mixture inverted gently 2–3 times to mix. The medium is poured into 150 mm plates using 50–70 ml per plate and stored at 5° C. until use.

Just prior to use, twelve holes per plate are made in the agar. 25 µl of supernatant from fermentation of each strain is added to one plate of each pH and incubated overnight at 37° C. To pH 9 plates, 0.5M glacial acetic acid is added to precipitate casein and allow visualization of any clear zones. Each plate is then evaluated on clear zone size (i.e., from no zone to >2 cm in diameter) and zone type (i.e., clear, opaque or both types).

The supernatants of each culture are also used to evaluate the strains extracellular protein production. Novex (San Diego, Calif.) 8–16% gradient gels, prepared according to manufacturer's instructions, are used to assess the protein profile. A 75 µl (3 and 5 day) sample of culture supernatant is mixed with 20 µl of 5×dissociation buffer (dissociation buffer=4 ml 1M TriS-HCl, pH 6.8, 1 g SDS, 617 mg dithiothreitol, and sterile distilled water to 10 ml), and glycerol/bromophenol blue (10–20 mg added to about 10 ml of 80–90% glycerol, and placed in boiling water for 1–2 hours to dissolve), boiled for 5 minutes, cooled, loaded and run at 60–200 V until the bromphenol blue tracking dye reaches the bottom of the gel. The gels are silver stained according to the Biorad Silver Stain Plus Protocol (Biorad Laboratories, Hercules, Calif.). Those isolates showing large numbers of bands are considered less suitable as potential new hosts, while those showing relatively clean profiles with only 1–4 major bands are considered for further testing.

When the combined results of the protease assay and protein profile are reviewed, the majority of suitable potential candidates are found among the members of the section Nigri. Based on these results, the following isolates are selected for transformation studies: *A. japonicus* A1438 (CBS 568.65), *A. aculeatus* N1136 (CBS 101.43), *A. aculeatus* A1454 (CBS 172.66), *A. aculeatus* A1455 (CBS 186.67), *A. japonicus* var. *aculeatus* N0956 (IAM 13871), *A. phoenicis* A528 (CBS 139.48), *A. phoenicis* A530 (CBS 137.52), *A. phoenicis* E419 (CBS 137.52), *A. carbonarius* A3993 (IBT 4977), *A. carbonarius* ATCC 1025, *A. tamarii* E112 (ATCC 10836), *A. tamarii* N2266 (IFO 4358), and *A. tamarii* N2267 (IFO 4142). These cultures are also maintained as part of the Novo Nordisk Biotech Culture Collection, Davis, Calif.

II. Vector construction

A. Selectable marker vectors.

The vectors pJaL77 and pJaL154 are used in transformation of host cells with the hygromycin B resistance selectable marker. This marker is based on the *E. coli* hygromycin B phosphotransferase gene, which is under the control of the TAKA promoter in pJaL 77 and the amdS promoter in pJaL154. Briefly, these vectors are constructed as follows. The gene conferring resistance to hygromycin B is purchased from Boehringer Mannheim as plasmid pHph-1. This gene is equipped with an ATG codon as well as with suitable restriction sites at the amino and carboxy termini by PCR, using the primers: 5'-GCT CAG AAGCTT CCATCC TAC ACC TCA GCA ATG TCG CCT GAA CTC ACC GCG ACG TCT-3' (N-terminal (SEQ ID NO 7)) and 3'-CGT CCG AGG GCA AAG GAA TAG CTCCAG AGATCT CAT GCT-5' (C-terminal (SEQ ID NO 8)). The PCR fragment is cut with the restriction enzymes BamHI and XhoI and cloned into the corresponding sites in the Aspergillus expression vector pToC68 (as described in WO 91/17243) to produce pJaL77.

Plasmid pJaL154 is constructed as follows. The amdS promoter mutant $I_9+I_{666}$ (Hynes et al. Mol. Cell. Biol. 3(8): 1430–1439, 1983 and Katz et al. Mol Gen Genet. 220: 373–376, 1990) is cloned from plasmid pCaHj406 by PCR with the following primers (underlined regions represent homology to the amdS promoter: CCT GGA TCC TCT GTG TTA GCT TAT AG (SEQ ID NO 9) and CTT GCA TGC CGC CAG GAC CGA GCA AG (SEQ ID NO 10). The 694 bp PCR fragment containing the amdS promoter is cut with BamHI and SphI and cloned into the corresponding site in pJaL77, so that the TAKA promoter in pJaL77 is exchanged with the amdS promoter. The plasmid pToC90 containing the amdS marker is constructed by cloning a 2.7 kb XbaI fragment from p3SR2 (Hynes et al., supra) into an XbaI cut and dephosphorylated pUC19 plasmid. The derivative designated pToC186 is identical to pToC90 except that the promoter region contains two mutations ($I_9$ and $I_{666}$) known to enhance expression of the amdS gene (Hynes et al., supra; Corrick et al., Gene 53: 63–71, 1987).

B. Expression vectors.

1. *Candida antarctica* lipase.

For expression of *Candida antarctica* lipase A, chromosomal DNA of the *C. antarctica* strain LF058 (DSM 3855) is extracted according to the methosd of Yelton et al. (PNAS U.S.A. 81: 1470–1474, 1984) The purified DNA is cut partially with Sau3A and after agarose gel electrophoresis, fragments in the range of 3–9 kb are isolated. The sized Sau3A fragments are ligated into a BamHI-cut, dephosphorylated plasmid pBR322 (New England Biolabs). The ligation mix is transformed into *E. coli* MT172. About 50,000 *E. coli* transformants are obtained, 80% of which contain an in insert of LF058 DNA.

By standard colony hybridization techniques, the colonies are screened with the $^{32}$P-phosphorylated oligonucleotide probe NOR 440, a degenerate 17 mer based on the N-terminal sequence determined from mature *C. antarctica* lipase. 34 colonies appear positive after wash at low stringency(41° C. and 6×SSC). Plasmids were prepared from these colonies and analyzed by southern hybridization after restriction with BstNI. The probe for the southern is either the NOR 440 probe used for colony hybridization or a $^{32}$P-labelled probe NOR 438. NOR 438 is an oligonucleotide corresponding to amino acid sequence of the lipase in which, at 13 positions, a base has been chosen on the basis of codon use in yeasts and filamentous fungi.

```
AACCCATACGACGACCC              NOR 440(SEQ ID NO 11)
   T  C   T  T  T
         G
         T
```

```
                               NOR 438(SEQ ID NO 12)
GCTGCTCTGCCTAACCCTTACGACGACCCTTTCTACACCACCCC
   -  -  -        -         -   T  T  T   -  -
```

Guess positions are indicated.

Only one plasmid, pMT1076, contains a band which hybridizes both to NOR 440 at low stringency and to NOR 438 at somewhat higher stringency (55° C. and 1×SSC).

pMT1076 is restriction mapped and the sequence determined by the Maxam-Gilbert method. The sequence is shown in Seq. ID NO. 1. The open reading frame is seen to encode a putative signal of 21 amino acids and also a propeptide of 10 amino acids preceding the N-terminal of the mature lipase. The last two amino acids of the propeptide are Arg, Arg, a typical cleavage site for endoproteolytic processing by enzymes of the *S. cerevisiae* KEX-2 type. The amino acid sequence is depicted in Seq. ID. No. 2. Through a number of standard plasmid manipulations (Maniatis et al., Molecular Cloning. Cold Spring Harbor, N.Y., 1982), the open reading frame of *C. antarctica* lipase A is placed in the correct orientation between the alpha-amylase promoter of *A. oryzae* and the glucoamylase transcription terminator of *A. niger*. The resulting expression plasmid is pMT1229.

2. *Humicola insolen* ylanase.

The vector pHD414 is a derivative of the plasmid p775 (EP 238 023). In contrast to this plasmid, pHD414 has a string of unique restriction sites between the TAKA promoter and the AMG terminator. The plasmid is constructed by removal of an approximately 200 bp long fragment (containing undesirable RE sites) at the 3' end of the terminator, and subsequent removal of an approximately 250 bp long fragment at the 5' end of the promoter, also containing undesirable sites. The 200 bp region is removed by cleavage with NarI (positioned in the pUC vector) and XbaI (just 3' to the terminator), subsequent filling in the generated ends with Klenow DNA polymerase+dNTP, purification of the vector fragment on a gel and religation of the vector fragment. This plasmid is called pHD413. pHD413 is cut with StuI (positioned in the 5' end of the promoter) and PvuII (in the pUC vector), fractionated on gel and religated, resulting in pHD414. A strain of *E. coli* containing the approximately 1,100 bp xylanase HindIII/XbaI CDNA fragment in pYES is deposited in DSM as DSM 6995. The xylanase cDNA fragment is isolated from one of the clones by cleavage with HindIII/XbaI. The fragment is purified by agarose gel electrophoresis, electroeluted, and made ready for ligation reactions. The cDNA fragment is ligated into pHD414 to produce pAXX40-1-1 The sequence of the xylanase gene and protein are provided in SEQ ID NOS 3 and 4, and the gene is deposited as DSM (Deutsche Sammlung Von Mikrooroganismen und Zellkulturen GmbH) 6995.

3. *Humicola insolens* cellulase.

Detailed characterization of the *Humicola insolens* cellulase is found in WO 91/17243. The expression vector pCaHj418 used for cellulase expression is constructed by excision of the 926 bp cellulase coding region fragment from pCaHj201 by cleavage with restriction enzymes BamHI and SalI. This fragment is purified by preparative gel electrophoresis using standard techniques and ligated with pHD414 (described above) which has been prepared by treatment with BamHI and XhoI. The resulting expression vector, pCaHj418, contains the cellulase gene under the transcriptional control of the *A. oryzae* taka-amylase promoter and the *A. niger* glucoamylase terminator region.

4. *Humicola lanuginosa* lipase.

Isolation and expression of the *H. lanuginosa* lipase gene is reported in EP 305 216, and in U.S. Ser. No. 07/236,605, the contents of which are incorporated herein by reference. Briefly, Total RNA is extracted from homogenized *H. lanuginosa mycelium* using methods as described by Boel et al. (EMBO J. 3: 1097–1102, 1984) and Chirgwin et al. (Biochemistry 18: 5294–5299, 1979). Poly(A)-containing RNA is obtained by two cycles of affinity chromatography on oligo(dT)-cellulose as described by Aviv and Leder (PNAS U.S.A. 69: 1408–1412, 1972). cDNA is synthesized with the use of methods described by Okayama and Berg (Molec. Cell. Biol. 2: 161–170, 1982), and with the vectors pSP62-K2 and pCDVI-PL described by Noma et al. (Nature 319: 640–646, 1986). The synthesized cDNA is transformed into a hsdR$^-$, M$^+$ derivative of *E. coli* MC1000 (Casadaban and Cohen. J. Mol. Biol. 138: 179–207, 1980) to generate recombinant clones.

A mixture of 32 pentadecamer oligodeoxyribonucleotides (SEQ ID NO 11 )

```
      A  A   A  A   A
d( TT AA TG TT AA),
      G  G   G  G   G
``` one of which is complementary to *H. lanuginosa* lipase mRNA in the region coding for Phe-Asn-Gln-Phe-Asn is synthesized on an Applied Biosystems, Inc. DNA synthesizer and purified by PAGE. Approximately 10,000 *E. coli* recombinants from the *H. lanuginosa* cDNA library are transferred to Whatman 540 paper filters. The colonies are lysed and innnobilized as described by Gergen et al. (Nucleic Acids Res. 7: 2115–2135, 1979). The filters are hybridized with the $^{32}$P-labelled *H. lanuginosa* lipase-specific pentadecamer mixture as described by Boel et al.(EMBO J. 3: 1097–1102, 1984). Hybridization and washing of the filters are done at 37° C. and 43° C., respectively, followed by autoradiography for 24 hours with an intensifier screen. Miniprep plasmid DNA is isolated from two hybridizing colonies, pHLL 702.3 and pHLL 702.4 by standard procedures (Birnboim and Doly, Nucleic Acids Res. 7: 1513–1523, 1979) and the DNA sequence of the DNA insert is established by the procedure of Maxam and Gilbert (Methods Enzymol. 65: 499–560, 1980).

To facilitate further construction work with the cDNA, DNA sequences containing unique restriction sites are added to the 5' and 3' ends of the cDNA as follows. pHLL 702.3 is digested with Sau961 which digests the cDNA in the 3' untranslated region and the resulting ends are filled in with *E. coli* DNA polymerase(Klenow fragment) and the four dNTPs. This DNA is subsequently digested with SacI which cuts the cDNA once just 3' to the initiating methionine codon. The resulting 0.9 kb cDNA fragment is purified by agarose gel electrophoresis; electroeluted and made ready for ligation reactions. As a 5' adaptor two oligonucleotides, 927 and 928, are synthesized. This adaptor is designed to add a HindIII and BamHI site just 5' to the initiating Met codon of the cDNA. The two oligos are kinased with ATP and T4 polynucleotide kinase, annealed to each other and ligated to the purified 0.9 kb cDNA sequence in a pUC19 vector digested with HindIII and HincII and purified on a 0.7% agarose gel. The resulting plasmid carries the *H. lanuginosa* lipase cDNA as a portable 0.9 kb BamHI fragment. After BamHI digestion and purification of the 0.9 kb cDNA fragment on an agarose gel, it is ligated to BamHI and phosphatased p775 to generate p960 in which the lipase cDNA is under transcriptional control of the TAKA promoter from *A. oryzae* and the AMG terminator from *A. niger*.

To prepare pMHan37, p960 is modified by replacing 60 basepairs of the 5'untranslated region of the *A. oryzae* TAKA promoter just upstream to the *Humicola lanuginosa* lipase gene by the corresponding region from the *A. nidulans* tpiA gene (McKnight et al. Cell 46: 143–147, 1986). A synthetic oligonucleotide containing the 5' untranslated region from the *A. nidulans* tpiA flanked at each end by 20 bases homologous to p960 sequences just outside the untranslated region is used in a PCR reaction together with another primer covering the BssHII-site in the TAKA promoter region, as the mutagenization primer covers the BamHI site close to the ATG start codon, the PCR fragment is digested with BamHI and BSSHII and recloned into p960 digested with BssHII and partially with BamHI. 200 bases upstream to the ATG in MHan37 is verified by DNA sequencing analysis. The sequence difference between p960 and pMHan37 is shown below:

from the *Coprinus cinereus* cDNA library are transferred to Whatman 540 paper filters. The colonies are lysed and immobilized as described by Gergen et al. (Nucleic Acids Res. 7: 2115–2135, 1979). The filters are hybridized with the $^{32}$P-labelled 430 base pair peroxidase-specific probe in 0.2×SSC, 0.1% SDS. Hybridization and washing of the filters is conducted at 65° C. followed by autoradiography for 24 hours with an intensifier screen. After autoradiography, the filters are washed at increasing temperatures followed by autoradiography for 24 hours with an intensifier screen. In this way, more than 50 positive clones are identified. Miniprep plasmid DNA is isolated from hybridizing colonies by standard procedures (Birnboim and Doly, Nucleic Acids Res. 7: 1513–1523, 1979) and the DNA sequence of the cDNA insert is determined by the Sanger dideoxy procedure (Sanger et al., PNAS U.S.A. 74: 5463–5467, 1977). The peroxidase cDNA fragment is excised from the vector by cleavage with HindIII/XhoI and is purified by agarose gel electrophoresis, electroeluted and made ready for ligation reactions. The cDNA fragment is ligated to HindIII/XhoI digested HD414 to generated pCip in which the cDNA is under transcriptional control of the TAKA promoter from *A. oryzae* and the AMG terminator from *A. niger*. pJVi9 is prepared from pCiP in that the restriction sites for SacI, KpnI, HindIII, PstI, SalI, and BamHI immediately preceding the peroxidase start codon are deleted.

The cDNA sequence encoding the *Coprinus cinereus* peroxidase is shown in SEQ ID NO. 5 and 6.

A summary of the expression vectors prepared is provided in Table 1.

| | |
|---|---|
| pMHan37 | CATGCTTGGAGTTTCCAACTCAATTTACCTCTATCCACACTTCTCTT |
| P960 | CATGCTTGGAG ... GATAGCAACCGACAACATCACATCAAGCTCTCC |
| pMHan37 | CCTTCCTCAACAATAAACCCCACAGGGG ... GGATCC (SEQ ID NO 14) |
| p960 | CTTCTCTGAATCCTCTATATACACAACTGGGGATCC (SEQ ID NO 15) |

The sequence of the primer covering the BamHI site:

5' GCTCCTCATGGTGGATCCCCAGTTGTGTATATAGACCATTGAGGAAGGAAGA
GAAGTGTGGATAGAGGTAAATTGAGTTGGAAACTCCAAGCATGGCATCCCTTGC 3' (SEQ ID NO 16)

5. *Coprinus cinereus* peroxidase.

The isolation and cloning of the *Coprinus cinereus* peroxidase gene is described in WO 92/16634. Briefly, total RNA is extracted from homogenized *Coprinus cinereus* (IFO 8371) mycelium, collected at the time of maximum peroxidase activity as described by Boel et al. (EMBO J. 3: 1097–1102, 1984) and Chirgwin et al. (Biochemistry 18: 5294–5299, 1979). Poly(A)-containing RNA is obtained by two cycles of affinity chromatography on oligo(dT)-cellulose as described by Aviv and Leder (PNAS U.S.A. 69: 1408–1412, 1972). cDNA is synthesized by means of a cDNA synthesis kit from Invitrogen according to the manufacturer's instructions. About 50,000 *E. coli* recombinants

TABLE 1

Expression vectors used for co-transformation of new host candidates

| Vector | Gene encoded | Promoter | Terminator |
|---|---|---|---|
| pMHan37 | H. lanuginosa lipase (HLL) | TAKA-amylase | AMG |
| pAXX40-1-1 | H. insolens xylanase | TAKA-amylase | AMG |

TABLE 1-continued

Expression vectors used for co-transformation of new host candidates

| Vector | Gene encoded | Promoter | Terminator |
|---|---|---|---|
| pCaHj418 | H. insolens cellulase | TAKA-amylase | AMG |
| pJVi9 | Coprinus cinereus peroxidase (CiP) | TAKA-amylase | AMG |
| pMT1229 | Candida antarctica lipase A | TAKA-amylase | AMG |

III. Transformation of Aspergillus hosts

The following general procedures are used in transformation of all the strains tested, with exceptions noted expressly:

100 ml of MY50 medium is inoculated with spores of the strain to be transformed and incubated with shaking at 34° C. for 1–2 days. The mycelium was harvested by filtration through miracloth and washed with 200 ml of 0.6M $MgSO_4$. The mycelium is suspended in 15 ml of 1.2M $MgSO_4$, 10 mM $NaH_2PO_4$, pH=5.8. The suspension is cooled on ice and 1 ml of buffer containing 120 mg of Novozyme® 234 is added. After 5 minutes, 1 ml of 12 mg/ml BSA (Sigma type H25) is added and incubation with gentle agitation continued for 1.5–2.5 hours at 37° C. until a large number of protoplasts is visible in a sample inspected under the microscope. The suspension is filtered through miracloth, the filtrate is transferred to a sterile tube and overlaid with 5 ml of 0.6M sorbitol, 100 mM Tris-HCl, pH=7.0. Centrifugation is performed for 15 minutes at 2500 rpm and the protoplasts are collected from the top of the $MgSO_4$ cushion. Two volumes of STC (1.2M sorbitol, 10 mM Tris-HCl pH=7.5, 10 mM $CaCl_2$) are added to the protoplast suspension and the mixture is centrifuged for five minutes at 1000×g. The protoplast pellet is resuspended in 3 ml of STC and repelleted. This is repeated, and then the protoplasts are resuspended in 0.2–1 ml of STC.

100 μl of protoplast suspension is mixed with 5–25 μg of the appropriate DNA in 10 μl of STC. Each strain is cotransformed with an expression vector containing the structural gene of interest (see Table 1), and a plasmid containing a selectable marker. Plasmids pToC90 and pToC186 contain the A. nidulans amdS gene, and are used for transformation and selection for growth on acetamide as the sole nitrogen source. Plasmids pJaL77 and pJaL154 are used for transformation and selection of resistance to hygromycin B.

The mixtures are left at room temperature for 25 minutes. 0.2 ml of 60% PEG 4000 (BDH 29576), 10 mM $CaCl_2$ and 10 mM Tris-HCl pH=7.5 is added and carefully mixed twice and finally 0.85 ml of the same solution is added and carefully mixed. The mixture is left at room temperature for 25 minutes, spun at 2500×g for 15 minutes and the pellet resuspended in 2 ml of 1.2M sorbitol. After one more sedimentation the protoplasts are spread on the appropriate plates. Protoplasts are spread on minimal plates (Cove, Biochem. Biophys. Acta 113: 51–56, 1966) containing 1.0M sucrose, pH=7.0, 10 mM acetamide as nitrogen source (when amdS is the selection marker) and 20 mM CsCl to inhibit background growth. The medium differs when hygB is the selection marker in the use of 10 mM sodium nitrate as nitrogen source, and the presence of 150 μg/ml hygromycin B. As an alternate to the final centrifugation step, resuspending and spreading, 8 ml of STC can be added and mixed with the protoplasts, and 3 ml are added to each of 3 selection plates, which are then swirled to cover the plate. After incubation for 4–7 days at 37° C. colonies with conidia are picked, suspended in sterile water and spread for isolation of single colonies. This procedure is repeated and spores of a single colony after the second reisolation are stored as a defined transformant.

IV. Evaluation of recombinant protein expression

Following the above procedure, individual isolates of the selected strains are co-transformed with one of the exloression vectors noted in Table 1, and one of the plasmids containing a selectable marker mentioned in the preceding example. Each of the co-tranformants is then tested in the appropriate assay to determine expression of the gene of interest.

A. Lipase

Cotransformants for lipase activity are cultured in a M400Da medium consisting of 50 g/l maltodextrin, 2 g/l $MgSO_4 \cdot 7H_2O$, 2 g/l $KH_2PO_4$, 3 g/l $K_2SO_4$, 4 g/l citric acid, 8 g/l yeast extract, 3 g/l $(NH_4)_2SO_4$, 0.5 ml Trace metal solution, 4 ml 50% urea solution (autoclaved separately), in 1 liter of distilled water, pH 6.0, and 5 g/l yeast extract made up in tap water to 800 ml. pH is adjusted to 4.5 before autoclaving. After autoclaving, 166 ml filter sterilized 1M urea (to give a final concentration of 10 g/l) and 35.3 ml of filter sterilized 1M $NANO_3$ (to give a final concentration of 0.3%) are added.

Lipase activity in culture filtrates is measured using p-nitrophenylbutyrate (pNB) as a substrate. A stock solution of pNB is prepared by adding 104.6 μl of pNB to 5 ml of DMSO. To each well of a microtiter plate is added 90 μl of 50 mM Tris, pH 7. Ten μl of sample is added to each well, and mixed by shaking the microtiter plate for about one minute. Just prior to the assay, 20 μl of pNB stock is combined with 970 μl of 50 mM Tris buffer, pH 7 and mixed. Immediately prior to assaying for lipase activity using a commercial plate reader, 100 μl of the pNB-Tris mixture are added to each sample well and absorbance measured at 405 nm over a 3 minute time period. The assay is temperature sensitive, so an internal standard is used with each sample set. The slope determined for each sample directly correlates to lipase activity; the linear range of the assay is from about 0.005 to 5 μg lipase per milliliter. In this type of assay, the specific activity of H. lanuginosa lipase is determined to be approximately 4000 LU/mg, whereas the specific activity of Candida lipase A is about 400 LU/mg.

B. Xylanase

All xylanase transformants are grown in medium with the following composition, in g/l: maltodextrin, 50; $MgSo_4 \cdot 7H_2O$, 2.0; $KH_2PO_4$, 10.0; $K_2SO_4$, 2.0; citric acid 2.0; yeast extract, 10.0; AMG trace metal solution, 0.5 ml; urea, 2.0; pH 6.0. All the transformants are grown as submerged, agitiated cultures at 34° C.

Xylanase activity in culture broths is determined using 0.2% AZCL-xylan (Megazyme Co. Australia) suspended in a citrate phosphate buffer, pH 6.5. The culture fluid is diluted, usually 100-fold, and 10 μl of diluted culture fluid is mixed with 1 ml of 0.2% AZCL-xylan substrate. The mixture is incubated at 42° C. for 30 minutes. The reaction mixture is mixed well every 5 minutes. At the end of incubation, the undigested substrate is precipitated by centrifugation at 10,000 rpm for 5 minutes. The blue dye released from this substrate is quantified by absorbance at 595 nm and the amount of enzyme activity in the culture broths is calculated from a standard made with an enzyme preparation with known activity. An endoxylanase unit (EXU) is determined relative to an enzyme standard prepared under identical conditions.

C. Cellulase

Cellulase transformants are grown in MY50 medium (50 g/l maltodextrin, 2 g/l MgSO$_4$.7H$_2$O, 10 g/l KH$_2$PO$_4$, 2 g/l K$_2$SO$_4$, 2 g/l citric acid, 10 g/l yeast extract, 0.5 ml trace metals, 2.0 g urea, at 34° C. as submerged cultures.

Cellulase activity is measured using 0.2% AZCL-HE-cellulose (Megazyme) as a substrate suspended in 0.1M citrate-phosphate buffer at pH 6.5. The culture is diluted in 0.1M citrate buffer, pH 6.5, and 10 μl of diluted culture fluid is mixed with 1 ml of 0.2% AZCL-HE-cellulose. The mixture is incubated at 42° C. for 30 minutes with shaking every 5 minutes. After incubation, the undigested substrate is pelleted by centrifugation at 10,000 rpm for 5 minutes. The blue color in the supernatant is quantified spectrophotometrically at 595 nm, and the amount of enzyme activity is determined from a standard curve made with a known cellulase standard. Endocellulase units (ECU) are determined relative to an enzyme standard prepared under identical conditions.

D. Peroxidase

Cotransformants for CiP are cultured in a M400Da medium consisting of 50 g/l maltodextrin, 2 g/l MgSO$_4$.7H$_2$O, 2 g/l KH$_2$PO$_4$, 3 g/l K$_2$SO$_4$, 4 g/l citric acid, 8 g/l yeast extract, 3 g/l (NH$_4$)$_2$SO$_4$, 0.5 ml Trace metal solution, 4 ml 50% urea solution (autoclaved separately), in 1 liter of distilled water, pH 6.0.

Peroxidase expression is monitored using ABTS as a substrate or by rocket immunoelectrophoresis compared to a standard of known concentration. For immunodiffusion, 1% agarose in TM buffer (1.3 g/l Tris base, 0.6 g/l maleic acid, pH 7) is melted and cooled to 55° C. 400 μl of rabbit antiserum against CiP is mixed with 15 ml of agarose, spread and solidified on a 10 cm×10 cm plate. CDM agar(1 g/l K$_2$PO$_4$, 30 g/l sucrose, 0.3 g/l NANO$_3$, 0.05 g/l KCl, 0.05 g.l MgSO$_4$.7H$_2$O, 0.001 g/l FeSO$_4$.7H$_2$O, 0.001 g/l ZnSO$_4$.7H$_2$O, 0.0005 g/l CuSO$_4$.5H$_2$O, 20 g/l maltrodextrin, 15 g/l agarose) culture samples of tip transformants grown for 7 days at 37° C. in CDM are applied to 5 mm holes made in the agar plate. The protein is allowed to diffuse for 48 hours. The plate is stained with coomassie blue R to visualize the Protein-antibodyprecipitation zone. As a standard solution, purified is used at the concentrations of 500, 1000, and 2000 peroxidase units (PODU)/ml; 1 PODU is the amount of enzyme which under the standard conditions catalyzes the conversion of 1 μmol hydrogen peroxide per minute.

To determine peroxidase by the ABTS (2,2'-azinobis(3-ethylbenzothiazoline-6-sulfonate) method, 2 ml of 2 mM ABTS[0.110 g ABTS, Boehringer Mannheim No. 102946 in 0.1M phosphate buffer (10.63 g disodiumhydrogen phosphate dihydrate p.a. M6580, 5.49 potassium dihydrogenphosphate p.a. M4873 in demineralized water up to 1 liter) is preheated for 10 minutes at 30° C. To this is added 10.6 mM H$_2$O$_2$ solution(1.0 g Perhydrol Suprapur® 30% H$_2$O$_2$ Merck 7298 in demineralized water up to 25 ml), and 0.2 ml of sample or standard (standard=5.0 mg Kem-En-Tec, grade 1, No. 4140A in phosphate buffer up to 25 ml, diluted 400 times) in a glass tube. The reaction is conducted at 30° C. for three minutes. The absorbance of the sample is measured at 418 nm against milli Q demineralized water and followed for three minutes. The best reflection of peroxidase activity is given by the absorbance difference: $\Delta A = A_{(75\ sec)} - A_{(15\ sec)}$. The absorbance difference should lie between 0.15–0.30 corresponding to 0.05–0.1 PODU/ml in the sample.

VI. Results and Discussion

Table 2 summarizes the expression levels of various heterologous fungal enzymes produced by the alternative host of the present invention. It can be seen from the table that all strains were successful in expression of at least one of the genes of interest. In several cases, the new host strains give unexpectedly high levels of enzyme. For example, at least one strain of each of A. aculeatus, A. japonicus, and A. japonicus var. aculeatus yields surprisingly high levels of HLL in shake flask cultures (approximately one gram per liter), demonstrating that these species are capable of expressing large quantities of heterologous protein. In fact, the levels of production of HLL produced by these transformants appear to be as good as or better than the best primary transformants of A. oryzae.

A. japonicus also is shown to be an excellent host for the production of xylanase compared with A. oryzae and A. niger Bo80. The shake flask yields for this enzyme are approximately twice the levels seen for the best A. oryzae transformants.

A. aculeatus strain A1455 also shows good production of Candida antarctica lipase A, giving shake flask yields in the gram per liter range, which is about three to four times better than corresponding A. oryzae primary transformants grown under the same conditions.

TABLE 2

Expression of fungal enzymes in A. japonicus-type species

| Species/ strain | Selection | Gene expressed | No. transform. (No. positive) | Expression yield (shake flask) |
|---|---|---|---|---|
| A. aculeatus N1136 | amdS | CiP | 33(2) | 0.06 g/l |
|  | amdS | HLL | 25(2) | — |
|  | amdS | xylanase | 28(9) | 0.02–0.05 g/l |
|  | amdS | lipase A | 41(5) | — |
| A. aculeatus A1454 | amdS | Cellulase | 21(7) | 0.3 g/l |
| A. aculeatus A1455 | amdS | HLL | 28(21) | 1.0 g/l |
|  | amdS | lipase A | 15(14) | 1.0 g/l |
| A. japonicus A1438 | amdS | CiP | 11(6) | 0.05–0.1 g/l |
|  | amdS | HLL | 38(15) | 1.0–1.5 g/l |
|  | amdS | xylanase | 31(13) | 0.08 g/l |
|  | hygB | xylanase | 22(14) | 0.18 g/l |
|  | amdS | Cellulase | 42(28) | 0.5 g/l |
| A. japonicus var. aculeatus N0956 | amdS | HLL | 19(13) | 1.0 g/l |
|  | amdS | Cellulase | 26(7) | 0.2–0.3 g/l |
| A. oryzae A 1560 control (best primary transformant from over 20 screened) | amdS | CiP | control | 0.25 g/l |
|  | amdS | HLL | control | 1 g/l |
|  | amdS | Cellulase | control | 0.75–1 g/l |
|  | amdS | xylanase | control | 0.1 g/l |
|  | amdS | lipase A | control | 0.3 g/l |

As can be seen from the data presented, a number of strains of the japonicus-type species can produce substantial quantities of a variety of heterologous proteins, and therefore are established as being useful as alternatives to the standard A. niger and A. oryzae host systems, and in some cases may be preferable to the use of these known hosts.

Deposit of Biological Materials

The following biological materials have been deposited in Agricultural Research Service Culture Collection (NRRL) 1815 North University Street, Peoria, Ill. 61604.

| Cell line | Accession No. |
|---|---|
| *E. coli* DH5α containing pJVi9 | NRRL B-21161 |
| *E. coli* DH5α containing pCaHJ418 | NRRL B-21162 |
| *E. coli* DH5α containing pMT1229 | NRRL B-21163 |
| *E. coli* DH5α containing pAXX40-1-1 | NRRL B-21164 |
| *E. coli* DH5α containing pMHan37 | NRRL B-21165 |

What we claim is:

1. An *Aspergillus japonicus*-type host cell comprising a nucleic acid sequence encoding a heterologous protein operably linked to a promoter.

2. The host cell of claim 1 in which the protein is a fungal protein.

3. The host cell of claim 2 in which the promoter is a fungal promoter.

4. The host cell of claim 2 in which the protein is a fungal enzyme.

5. The host cell of claim 4 in which the enzyme is selected from the group consisting of a catalase, laccase, phenoloxidase, oxidase, oxidoreductases, cellulase, xylanase, peroxidase, lipase, hydrolase, esterase, cutinase, protease and other proteolytic enzymes, aminopeptidase, carboxypeptidase, phytase, lyase, pectinase and other pectinolytic enzymes, amylase, glucoamylase, α-galactosidase, β-galactosidase, α-glucosidase, β-glucosidase, mannosidase, isomerase, invertase, transferase, ribonuclease, chitinase, and deoxyribonuclease.

6. The host cell of claim 1 which also comprises a selectable marker.

7. The host cell of claim 6 in which the marker is a selected from the group consisting of argB, trpC, pyrG, amdS, and hygB.

8. The host cell of claim 2 in which the promoter is selected from the group consisting of the promoters from *A. oryzae* TAKA amylase, *Rhizomucor miehei* aspartic proteinase, *A. niger* glucoamylase, *A. niger* neutral α-amylase, *A. niger* acid stable α-amylase, and *Rhizomucor miehei* lipase.

9. The host cell of claim 1 which is a member of the species *A. japonicus*, *A. aculeatus* or *A. japonicus* var. *aculeatus*.

10. An *Aspergillus japonicus*-type host cell comprising a nucleic acid sequence encoding a heterologous fungal enzyme operably linked to a fungal promoter, and a selectable marker.

11. The host cell of claim 10 which comprises a fungal enzyme selected from the group consisting of a lipase, a xylanase and a cellulase.

12. The host cell of claim 10 in which the promoter is selected from the group consisting of the promoters from *A. oryzae* TAKA amylase, *Rhizomucor miehei* aspartic proteinase, *A. niger* glucoamylase, *A. niger* neutral α-amylase, *A. niger* acid stable α-amylase, and *Rhizomucor miehei* lipase.

13. The host cell of claim 12 in which the selectable marker is selected from the group consisting of argB, trpC, pyrG, amdS, and hygB.

14. The host cell of claim 10 in which the host cell is a member of the species *A. japonicus*, *A. aculeatus* or *A. japonicus* var. *aculeatus*.

15. The host cell of claim 10 which is an *A. japonicus* host cell comprising a nucleic acid sequence encoding a fungal xylanase, operably linked to a TAKA-amylase promoter, and further comprising an amdS or hygB marker.

16. The host cell of claim 10 which is an *A. japonicus* var. *aculeatus* host cell comprising a nucleic acid sequence encoding a fungal lipase, operably linked to a TAKA-amylase promoter or an AMG promoter, and further comprising an amdS marker.

17. The host cell of claim 10 which is an *A. aculeatus* host cell comprising a nucleic acid sequence encoding a fungal lipase, operably linked to a TAKA-amylase promoter and further comprising an amdS marker.

18. A method for producing a protein of interest which comprises culturing an *Aspergillus japonicus*-type host cell comprising a nucleic acid sequence encoding a heterologous protein operably linked to a promoter, under conditions which permit expression of the protein, and recovering the protein from culture.

19. The method of claim 18 in which the protein is a fungal protein.

20. The method of claim 19 in which the promoter is a fungal promoter.

21. The method of claim 20 in which the protein is a fungal enzyme.

22. The method of claim 21 in which the enzyme is selected from the group consisting of a catalase, laccase, phenoloxidase, oxidase, oxidoreductases, cellulase, xylanase, peroxidase, lipase, hydrolase, esterase, cutinase, protease and other proteolytic enzymes, aminopeptidase, carboxypeptidase, phytase, lyase, pectinase and other pectinolytic enzymes, amylase, glucoamylase, α-galactosidase, β-galactosidase, α-glucosidase, β-glucosidase, mannosidase, isomerase, invertase, transferase, ribonuclease, chitinase, and deoxyribonuclease.

23. The method of claim 18 which also comprises a selectable marker.

24. The method of claim 23 in which the marker is a selected from the group consisting of argB, trpC, pyrG, amdS, and hygB.

25. The method of claim 19 in which the promoter is selected from the group consisting of the promoters from *A. oryzae* TAKA amylase, *Rhizomucor miehei* aspartic proteinase, *A. niger* glucoamylase, *A. niger* neutral α-amylase, *A. niger* acid stable α-amylase, and *Rhizomucor miehei* lipase.

26. The method of claim 18 in which the host cell is a member of the species *A. japonicus, A. aculeatus* or *A. japonicus* var. *aculeatus*.

27. An *Aspergillus japonicus*-type host cell comprising a recombinant nucleic acid sequence encoding a homologous protein operably linked to a promoter.

28. A method for producing a protein of interest which comprises culturing an *Aspergillus japonicus*-type host cell comprising a recombinant nucleic acid sequence encoding a homologous protein operably linked to a promoter, under conditions which permit expression of the protein, and recovering the protein from culture.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 1389 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Candida antarctica
        ( C ) INDIVIDUAL ISOLATE: DSM 3855

( i x ) FEATURE:
        ( A ) NAME/KEY: CDS
        ( B ) LOCATION: 1..1389

( x i ) SEQUENCE DESCRIPTION: SEQ ID NO:1:

```
ATG CGA GTG TCC TTG CGC TCC ATC ACG TCG CTG CTT GCG GCG GCA ACG      48
Met Arg Val Ser Leu Arg Ser Ile Thr Ser Leu Leu Ala Ala Ala Thr
 1               5                  10                  15

GCG GCT GTG CTC GCG GCT CCG GCG GCC GAG ACG CTG GAC CGA CGG GCG      96
Ala Ala Val Leu Ala Ala Pro Ala Ala Glu Thr Leu Asp Arg Arg Ala
                20                  25                  30

GCG CTG CCC AAC CCC TAC GAC GAT CCC TTC TAC ACG ACG CCA TCC AAC     144
Ala Leu Pro Asn Pro Tyr Asp Asp Pro Phe Tyr Thr Thr Pro Ser Asn
            35                  40                  45

ATC GGC ACG TTT GCC AAG GGC CAG GTG ATC CAA TCT CGC AAG GTG CCC     192
Ile Gly Thr Phe Ala Lys Gly Gln Val Ile Gln Ser Arg Lys Val Pro
        50                  55                  60

ACG GAC ATC GGC AAC GCC AAC AAC GCT GCG TCG TTC CAG CTG CAG TAC     240
Thr Asp Ile Gly Asn Ala Asn Asn Ala Ala Ser Phe Gln Leu Gln Tyr
 65                  70                  75                  80

CGC ACC ACC AAT ACG CAG AAC GAG GCG GTG GCC GAC GTG GCC ACC GTG     288
Arg Thr Thr Asn Thr Gln Asn Glu Ala Val Ala Asp Val Ala Thr Val
                85                  90                  95

TGG ATC CCG GCC AAG CCC GCT TCG CCG CCC AAG ATC TTT TCG TAC CAG     336
Trp Ile Pro Ala Lys Pro Ala Ser Pro Pro Lys Ile Phe Ser Tyr Gln
                100                 105                 110

GTC TAC GAG GAT GCC ACG GCG CTC GAC TGT GCT CCG AGC TAC AGC TAC     384
Val Tyr Glu Asp Ala Thr Ala Leu Asp Cys Ala Pro Ser Tyr Ser Tyr
            115                 120                 125

CTC ACT GGA TTG GAC CAG CCG AAC AAG GTG ACG GCG GTG CTC GAC ACG     432
Leu Thr Gly Leu Asp Gln Pro Asn Lys Val Thr Ala Val Leu Asp Thr
        130                 135                 140
```

-continued

```
CCC  ATC  ATC  ATC  GGC  TGG  GCG  CTG  CAG  CAG  GGC  TAC  TAC  GTC  GTC  TCG        480
Pro  Ile  Ile  Ile  Gly  Trp  Ala  Leu  Gln  Gln  Gly  Tyr  Tyr  Val  Val  Ser
145                      150                      155                      160

TCC  GAC  CAC  GAA  GGC  TTC  AAA  GCC  GCC  TTC  ATC  GCT  GGC  TAC  GAA  GAG        528
Ser  Asp  His  Glu  Gly  Phe  Lys  Ala  Ala  Phe  Ile  Ala  Gly  Tyr  Glu  Glu
                    165                      170                      175

GGC  ATG  GCT  ATC  CTC  GAC  GGC  ATC  CGC  GCG  CTC  AAG  AAC  TAC  CAG  AAC        576
Gly  Met  Ala  Ile  Leu  Asp  Gly  Ile  Arg  Ala  Leu  Lys  Asn  Tyr  Gln  Asn
               180                      185                      190

CTG  CCA  TCC  GAC  AGC  AAG  GTC  GCT  CTT  GAG  GGC  TAC  AGT  GGC  GGA  GCT        624
Leu  Pro  Ser  Asp  Ser  Lys  Val  Ala  Leu  Glu  Gly  Tyr  Ser  Gly  Gly  Ala
          195                      200                      205

CAC  GCC  ACC  GTG  TGG  GCG  ACT  TCG  CTT  GCT  GAA  TCG  TAC  GCG  CCC  GAG        672
His  Ala  Thr  Val  Trp  Ala  Thr  Ser  Leu  Ala  Glu  Ser  Tyr  Ala  Pro  Glu
210                      215                      220

CTC  AAC  ATT  GTC  GGT  GCT  TCG  CAC  GGC  GGC  ACG  CCC  GTG  AGC  GCC  AAG        720
Leu  Asn  Ile  Val  Gly  Ala  Ser  His  Gly  Gly  Thr  Pro  Val  Ser  Ala  Lys
225                      230                      235                      240

GAC  ACC  TTT  ACA  TTC  CTC  AAC  GGC  GGA  CCC  TTC  GCC  GGC  TTT  GCC  CTG        768
Asp  Thr  Phe  Thr  Phe  Leu  Asn  Gly  Gly  Pro  Phe  Ala  Gly  Phe  Ala  Leu
                    245                      250                      255

GCG  GGT  GTT  TCG  GGT  CTC  TCG  CTC  GCT  CAT  CCT  GAT  ATG  GAG  AGC  TTC        816
Ala  Gly  Val  Ser  Gly  Leu  Ser  Leu  Ala  His  Pro  Asp  Met  Glu  Ser  Phe
               260                      265                      270

ATT  GAG  GCC  CGA  TTG  AAC  GCC  AAG  GGT  CAG  CGG  ACG  CTC  AAG  CAG  ATC        864
Ile  Glu  Ala  Arg  Leu  Asn  Ala  Lys  Gly  Gln  Arg  Thr  Leu  Lys  Gln  Ile
          275                      280                      285

CGC  GGC  CGT  GGC  TTC  TGC  CTG  CCG  CAG  GTG  GTG  TTG  ACC  TAC  CCC  TTC        912
Arg  Gly  Arg  Gly  Phe  Cys  Leu  Pro  Gln  Val  Val  Leu  Thr  Tyr  Pro  Phe
290                      295                      300

CTC  AAC  GTC  TTC  TCG  CTG  GTC  AAC  GAC  ACG  AAC  CTG  CTG  AAT  GAG  GCG        960
Leu  Asn  Val  Phe  Ser  Leu  Val  Asn  Asp  Thr  Asn  Leu  Leu  Asn  Glu  Ala
305                      310                      315                      320

CCG  ATC  GCT  AGC  ATC  CTC  AAG  CAG  GAG  ACT  GTG  GTC  CAG  GCC  GAA  GCG       1008
Pro  Ile  Ala  Ser  Ile  Leu  Lys  Gln  Glu  Thr  Val  Val  Gln  Ala  Glu  Ala
                    325                      330                      335

AGC  TAC  ACG  GTA  TCG  GTG  CCC  AAG  TTC  CCG  CGC  TTC  ATC  TGG  CAT  GCG       1056
Ser  Tyr  Thr  Val  Ser  Val  Pro  Lys  Phe  Pro  Arg  Phe  Ile  Trp  His  Ala
               340                      345                      350

ATC  CCC  GAC  GAG  ATC  GTG  CCG  TAC  CAG  CCT  GCG  GCT  ACC  TAC  GTC  AAG       1104
Ile  Pro  Asp  Glu  Ile  Val  Pro  Tyr  Gln  Pro  Ala  Ala  Thr  Tyr  Val  Lys
          355                      360                      365

GAG  CAA  TGT  GCC  AAG  GGC  GCC  AAC  ATC  AAT  TTT  TCG  CCC  TAC  CCG  ATC       1152
Glu  Gln  Cys  Ala  Lys  Gly  Ala  Asn  Ile  Asn  Phe  Ser  Pro  Tyr  Pro  Ile
370                      375                      380

GCC  GAG  CAC  CTC  ACC  GCC  GAG  ATC  TTT  GGT  CTG  GTG  CCT  AGC  CTG  TGG       1200
Ala  Glu  His  Leu  Thr  Ala  Glu  Ile  Phe  Gly  Leu  Val  Pro  Ser  Leu  Trp
385                      390                      395                      400

TTT  ATC  AAG  CAA  GCC  TTC  GAC  GGC  ACC  ACA  CCC  AAG  GTG  ATC  TGC  GGC       1248
Phe  Ile  Lys  Gln  Ala  Phe  Asp  Gly  Thr  Thr  Pro  Lys  Val  Ile  Cys  Gly
                    405                      410                      415

ACT  CCC  ATC  CCT  GCT  ATC  GCT  GGC  ATC  ACC  ACG  CCC  TCG  GCG  GAC  CAA       1296
Thr  Pro  Ile  Pro  Ala  Ile  Ala  Gly  Ile  Thr  Thr  Pro  Ser  Ala  Asp  Gln
               420                      425                      430

GTG  CTG  GGT  TCG  GAC  CTG  GCC  AAC  CAG  CTG  CGC  AGC  CTC  GAC  GGC  AAG       1344
Val  Leu  Gly  Ser  Asp  Leu  Ala  Asn  Gln  Leu  Arg  Ser  Leu  Asp  Gly  Lys
          435                      440                      445

CAG  AGT  GCG  TTC  GGC  AAG  CCC  TTT  GGC  CCC  ATC  ACA  CCA  CCT  TAG            1389
Gln  Ser  Ala  Phe  Gly  Lys  Pro  Phe  Gly  Pro  Ile  Thr  Pro  Pro
450                      455                      460
```

(2) INFORMATION FOR SEQ ID NO:2:

(i) SEQUENCE CHARACTERISTICS:
        (A) LENGTH: 462 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Val Ser Leu Arg Ser Ile Thr Ser Leu Leu Ala Ala Ala Thr
 1               5                  10                      15
Ala Ala Val Leu Ala Ala Pro Ala Ala Glu Thr Leu Asp Arg Arg Ala
             20                  25                  30
Ala Leu Pro Asn Pro Tyr Asp Asp Pro Phe Tyr Thr Thr Pro Ser Asn
             35                  40                  45
Ile Gly Thr Phe Ala Lys Gly Gln Val Ile Gln Ser Arg Lys Val Pro
         50                  55                  60
Thr Asp Ile Gly Asn Ala Asn Asn Ala Ala Ser Phe Gln Leu Gln Tyr
 65                  70                  75                  80
Arg Thr Thr Asn Thr Gln Asn Glu Ala Val Ala Asp Val Ala Thr Val
                 85                  90                  95
Trp Ile Pro Ala Lys Pro Ala Ser Pro Pro Lys Ile Phe Ser Tyr Gln
            100                 105                 110
Val Tyr Glu Asp Ala Thr Ala Leu Asp Cys Ala Pro Ser Tyr Ser Tyr
            115                 120                 125
Leu Thr Gly Leu Asp Gln Pro Asn Lys Val Thr Ala Val Leu Asp Thr
        130                 135                 140
Pro Ile Ile Ile Gly Trp Ala Leu Gln Gln Gly Tyr Tyr Val Val Ser
145                 150                 155                 160
Ser Asp His Glu Gly Phe Lys Ala Ala Phe Ile Ala Gly Tyr Glu Glu
                165                 170                 175
Gly Met Ala Ile Leu Asp Gly Ile Arg Ala Leu Lys Asn Tyr Gln Asn
            180                 185                 190
Leu Pro Ser Asp Ser Lys Val Ala Leu Glu Gly Tyr Ser Gly Gly Ala
        195                 200                 205
His Ala Thr Val Trp Ala Thr Ser Leu Ala Glu Ser Tyr Ala Pro Glu
    210                 215                 220
Leu Asn Ile Val Gly Ala Ser His Gly Gly Thr Pro Val Ser Ala Lys
225                 230                 235                 240
Asp Thr Phe Thr Phe Leu Asn Gly Gly Pro Phe Ala Gly Phe Ala Leu
                245                 250                 255
Ala Gly Val Ser Gly Leu Ser Leu Ala His Pro Asp Met Glu Ser Phe
            260                 265                 270
Ile Glu Ala Arg Leu Asn Ala Lys Gly Gln Arg Thr Leu Lys Gln Ile
        275                 280                 285
Arg Gly Arg Gly Phe Cys Leu Pro Gln Val Val Leu Thr Tyr Pro Phe
    290                 295                 300
Leu Asn Val Phe Ser Leu Val Asn Asp Thr Asn Leu Leu Asn Glu Ala
305                 310                 315                 320
Pro Ile Ala Ser Ile Leu Lys Gln Glu Thr Val Val Gln Ala Glu Ala
                325                 330                 335
Ser Tyr Thr Val Ser Val Pro Lys Phe Pro Arg Phe Ile Trp His Ala
            340                 345                 350
Ile Pro Asp Glu Ile Val Pro Tyr Gln Pro Ala Ala Thr Tyr Val Lys
```

|  |  |  |  |  | 355 |  |  |  |  | 360 |  |  |  |  | 365 |  |
|--|--|--|--|--|--|--|--|--|--|--|--|--|--|--|--|--|
| Glu | Gln | Cys | Ala | Lys | Gly | Ala | Asn | Ile | Asn | Phe | Ser | Pro | Tyr | Pro | Ile |
|  | 370 |  |  |  |  | 375 |  |  |  |  | 380 |  |  |  |  |

| Ala | Glu | His | Leu | Thr | Ala | Glu | Ile | Phe | Gly | Leu | Val | Pro | Ser | Leu | Trp |
|--|--|--|--|--|--|--|--|--|--|--|--|--|--|--|--|
| 385 |  |  |  |  | 390 |  |  |  |  | 395 |  |  |  |  | 400 |

| Phe | Ile | Lys | Gln | Ala | Phe | Asp | Gly | Thr | Thr | Pro | Lys | Val | Ile | Cys | Gly |
|--|--|--|--|--|--|--|--|--|--|--|--|--|--|--|--|
|  |  |  |  | 405 |  |  |  |  | 410 |  |  |  |  | 415 |  |

| Thr | Pro | Ile | Pro | Ala | Ile | Ala | Gly | Ile | Thr | Thr | Pro | Ser | Ala | Asp | Gln |
|--|--|--|--|--|--|--|--|--|--|--|--|--|--|--|--|
|  |  |  | 420 |  |  |  |  | 425 |  |  |  |  | 430 |  |  |

| Val | Leu | Gly | Ser | Asp | Leu | Ala | Asn | Gln | Leu | Arg | Ser | Leu | Asp | Gly | Lys |
|--|--|--|--|--|--|--|--|--|--|--|--|--|--|--|--|
|  |  | 435 |  |  |  |  | 440 |  |  |  |  | 445 |  |  |  |

| Gln | Ser | Ala | Phe | Gly | Lys | Pro | Phe | Gly | Pro | Ile | Thr | Pro | Pro |
|--|--|--|--|--|--|--|--|--|--|--|--|--|--|
|  | 450 |  |  |  |  | 455 |  |  |  |  | 460 |  |  |

(2) INFORMATION FOR SEQ ID NO:3:

(i) SEQUENCE CHARACTERISTICS:
        (A) LENGTH: 1123 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vi) ORIGINAL SOURCE:
        (A) ORGANISM: Humicola insolens
        (C) INDIVIDUAL ISOLATE: DSM 6995

(ix) FEATURE:
        (A) NAME/KEY: CDS
        (B) LOCATION: 126..806

(xi) SEQUENCE DESCRIPTION: SEQ ID NO:3:

```
AATACGACTC ACTATAGGGA ATATTAAGCT TGGTACCGAG CTCGGATCCA CTAGTAACGG        60

CCGCCAGTGT GCTCTAAAGC GCCGCTTCTT CAGTTGTGTA CGATCATCCA GCAACTCGCA       120
```

| GCACC | ATG | GTC | TCG | CTC | AAG | TCT | GTC | CTC | GCG | GCC | GCC | ACG | GCT | GTG | 167 |
|--|--|--|--|--|--|--|--|--|--|--|--|--|--|--|--|
|  | Met | Val | Ser | Leu | Lys | Ser | Val | Leu | Ala | Ala | Ala | Thr | Ala | Val |  |
|  | 1 |  |  |  | 5 |  |  |  |  | 10 |  |  |  |  |  |

| AGC | TCT | GCC | ATT | GCT | GCC | CCT | TTT | GAC | TTC | GTT | CCT | CGG | GAC | AAC | TCG | 215 |
|--|--|--|--|--|--|--|--|--|--|--|--|--|--|--|--|--|
| Ser | Ser | Ala | Ile | Ala | Ala | Pro | Phe | Asp | Phe | Val | Pro | Arg | Asp | Asn | Ser |  |
| 15 |  |  |  |  | 20 |  |  |  |  | 25 |  |  |  |  | 30 |  |

| ACG | GCC | CTT | CAG | GCT | CGA | CAG | GTG | ACC | CCC | AAC | GGC | GAG | GGC | TGG | CAC | 263 |
|--|--|--|--|--|--|--|--|--|--|--|--|--|--|--|--|--|
| Thr | Ala | Leu | Gln | Ala | Arg | Gln | Val | Thr | Pro | Asn | Gly | Glu | Gly | Trp | His |  |
|  |  |  |  | 35 |  |  |  |  | 40 |  |  |  |  | 45 |  |  |

| AAC | GGC | TAC | TTC | TAC | TCG | TGG | TGG | TCC | GAC | GGC | GGA | GGC | CAG | GTT | CAG | 311 |
|--|--|--|--|--|--|--|--|--|--|--|--|--|--|--|--|--|
| Asn | Gly | Tyr | Phe | Tyr | Ser | Trp | Trp | Ser | Asp | Gly | Gly | Gly | Gln | Val | Gln |  |
|  |  |  | 50 |  |  |  |  | 55 |  |  |  |  | 60 |  |  |  |

| TAC | ACC | AAC | CTC | GAG | GGC | AGC | CGC | TAC | CAG | GTC | AGA | TGG | CGT | AAC | ACC | 359 |
|--|--|--|--|--|--|--|--|--|--|--|--|--|--|--|--|--|
| Tyr | Thr | Asn | Leu | Glu | Gly | Ser | Arg | Tyr | Gln | Val | Arg | Trp | Arg | Asn | Thr |  |
|  |  | 65 |  |  |  |  | 70 |  |  |  |  | 75 |  |  |  |  |

| GGC | AAC | TTC | GTC | GGT | GGT | AAG | GGT | TGG | AAC | CCG | GGA | ACC | GGC | CGC | ACG | 407 |
|--|--|--|--|--|--|--|--|--|--|--|--|--|--|--|--|--|
| Gly | Asn | Phe | Val | Gly | Gly | Lys | Gly | Trp | Asn | Pro | Gly | Thr | Gly | Arg | Thr |  |
|  |  | 80 |  |  |  |  | 85 |  |  |  |  | 90 |  |  |  |  |

| ATC | AAC | TAC | GGC | GGC | TAC | TTC | AAC | CCC | CAG | GGC | AAC | GGC | TAC | CTG | GCC | 455 |
|--|--|--|--|--|--|--|--|--|--|--|--|--|--|--|--|--|
| Ile | Asn | Tyr | Gly | Gly | Tyr | Phe | Asn | Pro | Gln | Gly | Asn | Gly | Tyr | Leu | Ala |  |
| 95 |  |  |  |  | 100 |  |  |  |  | 105 |  |  |  |  | 110 |  |

| GTC | TAC | GGC | TGG | ACC | CGC | AAC | CCG | CTC | GTC | GAG | TAC | TAT | GTC | ATC | GAG | 503 |

```
Val Tyr Gly Trp Thr Arg Asn Pro Leu Val Glu Tyr Tyr Val Ile Glu
              115             120              125

TCG TAC GGC ACG TAC AAT CCC GGC AGC CAG GCT CAG TAC AAG GGC ACA    551
Ser Tyr Gly Thr Tyr Asn Pro Gly Ser Gln Ala Gln Tyr Lys Gly Thr
            130             135                 140

TTC TAT ACC GAC GGC GAT CAG TAT GAC ATC TTT GTG AGC ACC CGC TAC    599
Phe Tyr Thr Asp Gly Asp Gln Tyr Asp Ile Phe Val Ser Thr Arg Tyr
        145             150                 155

AAC CAG CCC AGC ATC GAC GGC ACC CGG ACG TTC CAG CAG TAC TGG TCT    647
Asn Gln Pro Ser Ile Asp Gly Thr Arg Thr Phe Gln Gln Tyr Trp Ser
    160             165                 170

ATC CGC AAG AAC AAG CGT GTC GGA GGC TCG GTC AAC ATG CAG AAC CAC    695
Ile Arg Lys Asn Lys Arg Val Gly Gly Ser Val Asn Met Gln Asn His
175             180                 185                     190

TTC AAC GCG TGG CAG CAG CAC GGA ATG CCG CTC GGC CAG CAC TAC TAC    743
Phe Asn Ala Trp Gln Gln His Gly Met Pro Leu Gly Gln His Tyr Tyr
                195             200                 205

CAG GTC GTC GCC ACC GAG GGC TAC CAG AGC AGT GGC GAG TCC GAC ATC    791
Gln Val Val Ala Thr Glu Gly Tyr Gln Ser Ser Gly Glu Ser Asp Ile
            210             215                 220

TAT GTT CAG ACA CAC TAAGCGACGC ACCCCGCATG ACAAAAGTCC GTTAGTTACA    846
Tyr Val Gln Thr His
            225

TGCCGGGTGA AAAGGAGCTA TGCTATGGGC GCGGCAAGAC AGTCACTGCC ATCATGTCAG  906

TCGGAAAAAC ATCGCAGAAT GGTGTTCTTC CGCATGGGAA TTGCCTGAGA CATCTCTCTG  966

GCCATGCATT TTCTTGTTCA TACTTGTTGG GCAGTCGCTT GGTTGCCTAC CTCTGTTTAT 1026

AGTCATTCTT TTTCTGTACA TACTTCTTCC TCAACTTTAG AGCACACTGG CGGCCGCTCG 1086

AGCATGCATC TAGAGGGCCG CATCATGTAA TTAGTTA                          1123
```

(2) INFORMATION FOR SEQ ID NO:4:

(i) SEQUENCE CHARACTERISTICS:
        (A) LENGTH: 227 amino acids
        (B) TYPE: amino acid
        (D) TOPOLOGY: linear (ii) MOLECULE TYPE: protein (xi) SEQUENCE DESCRIPTION: SEQ ID NO:4:

```
Met Val Ser Leu Lys Ser Val Leu Ala Ala Ala Thr Ala Val Ser Ser
 1               5                  10                  15

Ala Ile Ala Ala Pro Phe Asp Phe Val Pro Arg Asp Asn Ser Thr Ala
             20                  25                  30

Leu Gln Ala Arg Gln Val Thr Pro Asn Gly Glu Gly Trp His Asn Gly
         35                  40                  45

Tyr Phe Tyr Ser Trp Trp Ser Asp Gly Gly Gly Gln Val Gln Tyr Thr
     50                  55                  60

Asn Leu Glu Gly Ser Arg Tyr Gln Val Arg Trp Arg Asn Thr Gly Asn
65                  70                  75                  80

Phe Val Gly Gly Lys Gly Trp Asn Pro Gly Thr Gly Arg Thr Ile Asn
                 85                  90                  95

Tyr Gly Gly Tyr Phe Asn Pro Gln Gly Asn Gly Tyr Leu Ala Val Tyr
            100                 105                 110

Gly Trp Thr Arg Asn Pro Leu Val Glu Tyr Tyr Val Ile Glu Ser Tyr
            115                 120                 125

Gly Thr Tyr Asn Pro Gly Ser Gln Ala Gln Tyr Lys Gly Thr Phe Tyr
            130                 135                 140
```

```
Thr  Asp  Gly  Asp  Gln  Tyr  Asp  Ile  Phe  Val  Ser  Thr  Arg  Tyr  Asn  Gln
145                 150                     155                     160

Pro  Ser  Ile  Asp  Gly  Thr  Arg  Thr  Phe  Gln  Gln  Tyr  Trp  Ser  Ile  Arg
                    165                     170                     175

Lys  Asn  Lys  Arg  Val  Gly  Gly  Ser  Val  Asn  Met  Gln  Asn  His  Phe  Asn
               180                     185                     190

Ala  Trp  Gln  Gln  His  Gly  Met  Pro  Leu  Gly  Gln  His  Tyr  Tyr  Gln  Val
          195                     200                     205

Val  Ala  Thr  Glu  Gly  Tyr  Gln  Ser  Ser  Gly  Glu  Ser  Asp  Ile  Tyr  Val
     210                     215                     220

Gln  Thr  His
225
```

(2) INFORMATION FOR SEQ ID NO:5:

(i) SEQUENCE CHARACTERISTICS:
        (A) LENGTH: 1307 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Coprinus cinereus (ix) FEATURE:
        (A) NAME/KEY: CDS
        (B) LOCATION: 5..1096

(xi) SEQUENCE DESCRIPTION: SEQ ID NO:5:

```
TACT ATG AAG CTC TCG CTT TTG TCC ACC TTC GCT GCT GTC ATC ATC GGT         49
     Met Lys Leu Ser Leu Leu Ser Thr Phe Ala Ala Val Ile Ile Gly
     1               5                   10                  15

GCC CTC GCT CTA CCC CAG GGT CCT GGA GGA GGC GGG TCA GTC ACT TGC          97
Ala Leu Ala Leu Pro Gln Gly Pro Gly Gly Gly Gly Ser Val Thr Cys
                20                  25                  30

CCC GGT GGA CAG TCC ACT TCG AAC AGC CAG TGC TGC GTC TGG TTC GAC         145
Pro Gly Gly Gln Ser Thr Ser Asn Ser Gln Cys Cys Val Trp Phe Asp
                35                  40                  45

GTT CTA GAC GAT CTT CAG ACC AAC TTC TAC CAA GGG TCC AAG TGT GAG         193
Val Leu Asp Asp Leu Gln Thr Asn Phe Tyr Gln Gly Ser Lys Cys Glu
                50                  55                  60

AGC CCT GTT CGC AAG ATT CTT AGA ATT GTT TTC CAT GAC GCG ATC GGA         241
Ser Pro Val Arg Lys Ile Leu Arg Ile Val Phe His Asp Ala Ile Gly
    65                  70                  75

TTT TCG CCG GCG TTG ACT GCT GCT GGT CAA TTC GGT GGT GGA GGA GCT         289
Phe Ser Pro Ala Leu Thr Ala Ala Gly Gln Phe Gly Gly Gly Gly Ala
80                  85                  90                  95

GAT GGC TCC ATC ATT GCG CAT TCG AAC ATC GAA TTG GCC TTC CCG GCT         337
Asp Gly Ser Ile Ile Ala His Ser Asn Ile Glu Leu Ala Phe Pro Ala
                100                 105                 110

AAT GGC GGC CTC ACC GAC ACC GTC GAA GCC CTC CGC GCG GTC GGT ATC         385
Asn Gly Gly Leu Thr Asp Thr Val Glu Ala Leu Arg Ala Val Gly Ile
                115                 120                 125

AAC CAC GGT GTC TCT TTC GGC GAT CTC ATC CAA TTC GCC ACT GCC GTC         433
Asn His Gly Val Ser Phe Gly Asp Leu Ile Gln Phe Ala Thr Ala Val
         130                 135                 140

GGC ATG TCC AAC TGC CCT GGC TCT CCC CGA CTT GAG TTC TTG ACG GGC         481
Gly Met Ser Asn Cys Pro Gly Ser Pro Arg Leu Glu Phe Leu Thr Gly
```

```
                    145                         150                         155
AGG   AGC   AAC   AGT   TCC   CAA   CCC   TCC   CCT   CCT   TCG   TTG   ATC   CCC   GGT   CCC        529
Arg   Ser   Asn   Ser   Ser   Gln   Pro   Ser   Pro   Pro   Ser   Leu   Ile   Pro   Gly   Pro
160                           165                           170                           175

GGA   AAC   ACT   GTC   ACT   GCT   ATC   TTG   GAT   CGT   ATG   GGC   GAT   GCA   GGC   TTC        577
Gly   Asn   Thr   Val   Thr   Ala   Ile   Leu   Asp   Arg   Met   Gly   Asp   Ala   Gly   Phe
                          180                           185                           190

AGC   CCT   GAT   GAA   GTA   GTT   GAC   TTG   CTT   GCT   GCG   CAT   AGT   TTG   GCT   TCT        625
Ser   Pro   Asp   Glu   Val   Val   Asp   Leu   Leu   Ala   Ala   His   Ser   Leu   Ala   Ser
                      195                           200                           205

CAG   GAG   GGT   TTG   AAC   TCG   GCC   ATC   TTC   AGG   TCT   CCT   TTG   GAC   TCG   ACC        673
Gln   Glu   Gly   Leu   Asn   Ser   Ala   Ile   Phe   Arg   Ser   Pro   Leu   Asp   Ser   Thr
                  210                           215                           220

CCT   CAA   GTT   TTC   GAT   ACC   CAG   TTC   TAC   ATT   GAG   ACC   TTG   CTC   AAG   GGT        721
Pro   Gln   Val   Phe   Asp   Thr   Gln   Phe   Tyr   Ile   Glu   Thr   Leu   Leu   Lys   Gly
              225                           230                           235

ACC   ACT   CAG   CCT   GGC   CCT   TCT   CTC   GGC   TTT   GCA   GAG   GAG   CTC   TCC   CCC        769
Thr   Thr   Gln   Pro   Gly   Pro   Ser   Leu   Gly   Phe   Ala   Glu   Glu   Leu   Ser   Pro
240                           245                           250                           255

TTC   CCT   GGC   GAA   TTC   CGC   ATG   AGG   TCC   GAT   GCT   CTC   TTG   GCT   CGC   GAC        817
Phe   Pro   Gly   Glu   Phe   Arg   Met   Arg   Ser   Asp   Ala   Leu   Leu   Ala   Arg   Asp
                          260                           265                           270

TCC   CGA   ACC   GCC   TGC   CGA   TGG   CAA   TCC   ATG   ACC   AGC   AGC   AAT   GAA   GTT        865
Ser   Arg   Thr   Ala   Cys   Arg   Trp   Gln   Ser   Met   Thr   Ser   Ser   Asn   Glu   Val
                      275                           280                           285

ATG   GGC   CAG   CGA   TAC   NNN   NNN   NNC   ATG   GCC   AAG   ATG   TCT   GTT   CTC   GGC        913
Met   Gly   Gln   Arg   Tyr   Xaa   Xaa   Xaa   Met   Ala   Lys   Met   Ser   Val   Leu   Gly
                  290                           295                           300

TTC   GAC   AGG   AAC   GCC   CTC   ACC   GAT   TGC   TCT   GAC   GTT   ATT   CCT   TCT   GCT        961
Phe   Asp   Arg   Asn   Ala   Leu   Thr   Asp   Cys   Ser   Asp   Val   Ile   Pro   Ser   Ala
              305                           310                           315

GTG   TCC   AAC   AAC   GCT   GCT   CCT   GTT   ATC   CCT   GGT   GGC   CTT   ACT   GTC   GAT       1009
Val   Ser   Asn   Asn   Ala   Ala   Pro   Val   Ile   Pro   Gly   Gly   Leu   Thr   Val   Asp
320                           325                           330                           335

GAT   ATC   GAG   GTT   TCG   TGC   CCG   AGC   GAG   CCT   TTC   CCT   GAA   ATT   GCT   ACC       1057
Asp   Ile   Glu   Val   Ser   Cys   Pro   Ser   Glu   Pro   Phe   Pro   Glu   Ile   Ala   Thr
                          340                           345                           350

GCC   TCA   GGC   CCT   CTC   CCC   TCC   CTC   GCT   CCT   GCT   CCT   TGATCTCCTC                   1103
Ala   Ser   Gly   Pro   Leu   Pro   Ser   Leu   Ala   Pro   Ala   Pro
                      355                           360

AAGATGGTAC   ATCCTGCTCT   CTCATCATCC   CTCTTAGCTA   TTTATCCAAT   CTATCTACCT                         1163

ATCTATGCAG   TTTCTGTTCT   ATCACCACAG   GAAGCAAGAA   AGAAAAACAA   CAATGCAACG                         1223

TGAGCAGAAA   TCAGCAAAAA   AATAAATCAG   TATACTACAG   TAATGAGGCC   AGTTTGCGTG                         1283

GTGTCAGAAG   TAAGTACGAC   TCGG                                                                     1307
```

( 2 ) INFORMATION FOR SEQ ID NO:6:

( i ) SEQUENCE CHARACTERISTICS:
        ( A ) LENGTH: 363 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met   Lys   Leu   Ser   Leu   Leu   Ser   Thr   Phe   Ala   Ala   Val   Ile   Ile   Gly   Ala
  1                   5                          10                          15

Leu   Ala   Leu   Pro   Gln   Gly   Pro   Gly   Gly   Gly   Ser   Val   Thr   Cys   Pro
              20                          25                          30
```

| | | | | | | | | | | | | | | |
|---|---|---|---|---|---|---|---|---|---|---|---|---|---|---|
|Gly|Gly|Gln<br>35|Ser|Thr|Ser|Asn|Ser<br>40|Gln|Cys|Cys|Val|Trp<br>45|Phe|Asp|Val|
|Leu|Asp<br>50|Asp|Leu|Gln|Thr|Asn<br>55|Phe|Tyr|Gln|Gly|Ser<br>60|Lys|Cys|Glu|Ser|
|Pro<br>65|Val|Arg|Lys|Ile|Leu<br>70|Arg|Ile|Val|Phe|His<br>75|Asp|Ala|Ile|Gly|Phe<br>80|
|Ser|Pro|Ala|Leu|Thr<br>85|Ala|Ala|Gly|Gln|Phe<br>90|Gly|Gly|Gly|Gly|Ala<br>95|Asp|
|Gly|Ser|Ile|Ile<br>100|Ala|His|Ser|Asn|Ile<br>105|Glu|Leu|Ala|Phe|Pro<br>110|Ala|Asn|
|Gly|Gly|Leu<br>115|Thr|Asp|Thr|Val|Glu<br>120|Ala|Leu|Arg|Ala|Val<br>125|Gly|Ile|Asn|
|His|Gly<br>130|Val|Ser|Phe|Gly|Asp<br>135|Leu|Ile|Gln|Phe|Ala<br>140|Thr|Ala|Val|Gly|
|Met<br>145|Ser|Asn|Cys|Pro|Gly<br>150|Ser|Pro|Arg|Leu|Glu<br>155|Phe|Leu|Thr|Gly|Arg<br>160|
|Ser|Asn|Ser|Ser|Gln<br>165|Pro|Ser|Pro|Pro|Ser<br>170|Leu|Ile|Pro|Gly|Pro<br>175|Gly|
|Asn|Thr|Val|Thr<br>180|Ala|Ile|Leu|Asp|Arg<br>185|Met|Gly|Asp|Ala|Gly<br>190|Phe|Ser|
|Pro|Asp|Glu<br>195|Val|Val|Asp|Leu|Leu<br>200|Ala|Ala|His|Ser|Leu<br>205|Ala|Ser|Gln|
|Glu|Gly<br>210|Leu|Asn|Ser|Ala|Ile<br>215|Phe|Arg|Ser|Pro|Leu<br>220|Asp|Ser|Thr|Pro|
|Gln<br>225|Val|Phe|Asp|Thr|Gln<br>230|Phe|Tyr|Ile|Glu|Thr<br>235|Leu|Leu|Lys|Gly|Thr<br>240|
|Thr|Gln|Pro|Gly|Pro<br>245|Ser|Leu|Gly|Phe|Ala<br>250|Glu|Glu|Leu|Ser|Pro<br>255|Phe|
|Pro|Gly|Glu|Phe<br>260|Arg|Met|Arg|Ser|Asp<br>265|Ala|Leu|Leu|Ala|Arg<br>270|Asp|Ser|
|Arg|Thr|Ala<br>275|Cys|Arg|Trp|Gln|Ser<br>280|Met|Thr|Ser|Ser|Asn<br>285|Glu|Val|Met|
|Gly|Gln<br>290|Arg|Tyr|Xaa|Xaa|Xaa<br>295|Met|Ala|Lys|Met|Ser<br>300|Val|Leu|Gly|Phe|
|Asp<br>305|Arg|Asn|Ala|Leu|Thr<br>310|Asp|Cys|Ser|Asp|Val<br>315|Ile|Pro|Ser|Ala|Val<br>320|
|Ser|Asn|Asn|Ala|Ala<br>325|Pro|Val|Ile|Pro|Gly<br>330|Gly|Leu|Thr|Val|Asp<br>335|Asp|
|Ile|Glu|Val|Ser<br>340|Cys|Pro|Ser|Glu|Pro<br>345|Phe|Pro|Glu|Ile|Ala<br>350|Thr|Ala|
|Ser|Gly|Pro<br>355|Leu|Pro|Ser|Leu|Ala<br>360|Pro|Ala|Pro| | | | | |

( 2 ) INFORMATION FOR SEQ ID NO:7:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GCTCAGAAGC TTCCATCCTA CACCTCAGCA ATGTCGCCTG AACTCACCGC GACGTCT    57

( 2 ) INFORMATION FOR SEQ ID NO:8:

( i ) SEQUENCE CHARACTERISTICS:

(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:8:

TCGTACTCTA GAGACCTCGA TAAGGAAACG GGAGCCTGC  39

(2) INFORMATION FOR SEQ ID NO:9:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:9:

CCTGGATCCT CTGTGTTAGC TTATAG  26

(2) INFORMATION FOR SEQ ID NO:10:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:10:

CTTGCATGCC GCCAGGACCG AGCAAG  26

(2) INFORMATION FOR SEQ ID NO:11:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:11:

AA Y CCNTA Y G A-
Y GA Y CC  17

(2) INFORMATION FOR SEQ ID NO:12:

(i) SEQUENCE CHARACTERISTICS:
(A) LENGTH: 44 base pairs
(B) TYPE: nucleic acid
(C) STRANDEDNESS: single
(D) TOPOLOGY: linear (xi) SEQUENCE DESCRIPTION: SEQ ID NO:12:

GCTGCTCTGC CTAACCCTTA CGA Y GA Y CCT TTCTACACCA CCCC  44

(2) INFORMATION FOR SEQ ID NO:13:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:13:

RTTRAARTGR TTRAA  15

(2) INFORMATION FOR SEQ ID NO:14:

(i) SEQUENCE CHARACTERISTICS:
(A) LENGTH: 81 base pairs

-continued

```
      ( B ) TYPE: nucleic acid
      ( C ) STRANDEDNESS: single
      ( D ) TOPOLOGY: linear ( x i ) SEQUENCE DESCRIPTION: SEQ ID NO:14:

CATGCTTGGA  GTTTCCAACT  CAATTACCT  CTATCCACAC  TTCTCTTCCT  TCCTCAACAA        60

TAAACCCCAC  AGGGGGGATC  C                                                   81

( 2 ) INFORMATION FOR SEQ ID NO:15:

( i ) SEQUENCE CHARACTERISTICS:
         ( A ) LENGTH: 80 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:15:

CATGCTTGGA  GGATAGCAAC  CGACAACATC  ACATCAAGCT  CTCCTTCTC   TGAATCCTCT       60

ATATACACAA  CTGGGGATCC                                                      80

( 2 ) INFORMATION FOR SEQ ID NO:16:

( i ) SEQUENCE CHARACTERISTICS:
         ( A ) LENGTH: 106 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:16:

GCTCCTCATG  GTGGATCCCC  AGTTGTGTAT  ATAGACCATT  GAGGAAGGAA  GAGAAGTGTG       60

GATAGAGGTA  AATTGAGTTG  GAAACTCCAA  GCATGGCATC  CCTTGC                     106
```